(12) United States Patent
Hollis et al.

(10) Patent No.: US 8,790,673 B2
(45) Date of Patent: Jul. 29, 2014

(54) METHODS FOR TREATING ARTHROPODS

(75) Inventors: Shannon Hollis, Delaware, OH (US);
Casey McDonald, Galloway, OH (US);
Jason Rader, Marysville, OH (US)

(73) Assignee: OMS Investments, Inc., Los Angeles, CA (US)

( * ) Notice: Subject to any disclaimer, the term of this patent is extended or adjusted under 35 U.S.C. 154(b) by 1650 days.

(21) Appl. No.: 12/154,105

(22) Filed: May 20, 2008

(65) Prior Publication Data

US 2008/0221223 A1    Sep. 11, 2008

Related U.S. Application Data

(63) Continuation-in-part of application No. 11/801,466, filed on May 10, 2007, and a continuation-in-part of application No. 11/801,441, filed on May 10, 2007.

(60) Provisional application No. 60/800,545, filed on May 15, 2006, provisional application No. 60/800,531, filed on May 15, 2006.

(51) Int. Cl.
*A01N 25/02* (2006.01)
*A01N 25/00* (2006.01)
*A01N 25/32* (2006.01)
*A01N 31/14* (2006.01)

(52) U.S. Cl.
CPC ............. *A01N 25/02* (2013.01); *A01N 25/006* (2013.01); *A01N 25/32* (2013.01); *A01N 31/14* (2013.01)
USPC ............ 424/405; 424/406; 514/722; 514/723

(58) Field of Classification Search
CPC ...................................... A01N 31/14
USPC ......................................................... 514/723
See application file for complete search history.

(56) References Cited

U.S. PATENT DOCUMENTS

| 4,988,504 A | 1/1991 | Zotto et al. |
| 5,001,248 A | 3/1991 | Grabowski |

(Continued)

FOREIGN PATENT DOCUMENTS

| EP | 0943241 A1 | 9/1999 |
| JP | 07-206612 | 8/1995 |

(Continued)

OTHER PUBLICATIONS

Chandler, L.D. et al., Arthropod Management Tests, 20, pp. 353-354, (1995).

(Continued)

*Primary Examiner* — Neil Levy
(74) *Attorney, Agent, or Firm* — Hunton & Williams LLP

(57) ABSTRACT

Methods for treating arthropods comprising depositing at least one drop of a liquid formulation containing at least one surfactant on a solid surface of an arthropod at a contact angle sufficient to cause rapid and enhanced knockdown (KD) of the arthropod. The contact angle comprises an angle formed between a resting drop of the liquid formulation and the solid surface on which the drop rests measured, after a period of about 80 milliseconds (ms) or more from the time that a drop of the liquid formulation is deposited on the solid surface, at a contact point between a tangent line drawn on a liquid/vapor interface surface of the resting drop in contact with the solid surface and a tangent to the solid surface on which the drop rests.

2 Claims, 1 Drawing Sheet

(56) References Cited

U.S. PATENT DOCUMENTS

| | | | |
|---|---|---|---|
| 5,008,103 A | | 4/1991 | Raleigh et al. |
| 5,066,756 A | | 11/1991 | Raleigh et al. |
| 5,489,433 A | * | 2/1996 | Aboud .......................... 424/405 |
| 5,504,054 A | * | 4/1996 | Murphy ........................ 504/206 |
| 5,558,806 A | | 9/1996 | Policello et al. |
| 5,906,961 A | | 5/1999 | Roberts et al. |
| 5,998,331 A | | 12/1999 | Policello |
| 6,051,533 A | | 4/2000 | Kajikawa et al. |
| 6,063,771 A | * | 5/2000 | Snyder ............................ 514/31 |
| 6,124,301 A | | 9/2000 | Aven et al. |
| 6,221,811 B1 | | 4/2001 | Policello et al. |
| 6,327,813 B1 | | 12/2001 | Ishiwatari |
| 6,492,419 B1 | | 12/2002 | Shepherd |
| 6,717,019 B2 | | 4/2004 | Lassila |
| 6,734,141 B2 | | 5/2004 | Humble et al. |
| 6,992,045 B2 | | 1/2006 | Xu et al. |
| 7,278,294 B2 | | 10/2007 | Giles et al. |
| 2003/0013683 A1 | | 1/2003 | Holzer |
| 2003/0027792 A1 | * | 2/2003 | Ansell ............................ 514/63 |
| 2003/0104944 A1 | | 6/2003 | Humble et al. |
| 2005/0250805 A1 | | 11/2005 | Kannan et al. |
| 2007/0021304 A1 | | 1/2007 | Lin et al. |
| 2007/0031671 A1 | * | 2/2007 | Mizusaki et al. ............. 428/375 |
| 2007/0037712 A1 | * | 2/2007 | Mosko et al. ................. 504/358 |
| 2007/0142330 A1 | | 6/2007 | Ansell |
| 2007/0266749 A1 | | 11/2007 | Rader et al. |
| 2008/0038241 A1 | | 2/2008 | Schasfoort et al. |
| 2012/0329655 A1 | * | 12/2012 | Baseeth et al. ................ 504/206 |

FOREIGN PATENT DOCUMENTS

| | | |
|---|---|---|
| JP | 10-291903 | 4/1998 |
| JP | 11-322517 | 11/1999 |
| WO | WO 01/19190 A1 | 3/2001 |
| WO | WO 2007/136596 | 11/2007 |
| WO | WO 2007/136597 | 11/2007 |
| WO | WO 2008/110685 | 9/2008 |
| WO | WO 2009/143138 | 11/2009 |

OTHER PUBLICATIONS

Imai, T. et al., Appl. Entomol. Zool., vol. 30, pp. 380-382, Nov. 1994.
Srinivasan et al., Laboratory and Field Evaluation of Silwet L-77 and Kinetic Alone and in Combination with Imidacloprid and Abamectin for the Management of the Asian Citrus Psyllid, Diaphorina Citri (hemiptera: psyllidae) Florida Entemologist, Mar. 2008, pp. 87-200.
Liu and Stansly, Pest Management Science, vol. 56, 861-866, (2000).
Purcell, M.F. et al., Journal of Economic Entomology, vol. 89, pp. 1566-1570, Dec. 1996.
Shapiro, J.P. et al., Florida Entomologist, 81:, pp. 201-210, Jun. 1998.
Skinner, Arthropod Management Tests, 22, pp. 422, (1977).
Smitley and Davis, Arthropod Management Tests, vol. 22, pp. 385, (1997).
Tiiping et al., Journal of Economic Entomology, vol. 96, No. 1, 246-250 (2003).
Wood and Tedders, Hort. Science, vol. 32, pp. 1074-1076, Oct. 1997.
Woodward, "Dynamic Surface Tension and Dilational Stress Measurements Using the Drop Shape Method," pp. 1-6, (1999).
Woodward, "A Guide o FTA Video Drop Shape Software," pp. 1-4 (1999).
Woodward, "Contact Angle Measurements Using Drop Shape Method," pp. 1-8 (1999).
Zonyl Fluorosurfactants & Coating Additives, downloaded from the Internet at: http://www2.dupont.com/Zonyl_Foraperle/en_US/products/zonyl_pgs/surfactants.html, Mar. 18, 2008.
Siltech, LLC—Topical Report: Hydrolytic Stability Dimethicone Copolyols, © 2008.
SPI Supplies: Parafilm ® M Barrier Film, downloaded from the Internet at: http://www.2spi.com/catalog/supp/supp4b.shtml Feb. 6, 2008.
The Lipid Library: Waxes—Structure, Composition, Occurrence and Analysis, downloaded from the Internet at: http://www.lipidlibrary.co.uk/Lipids/waxes/index.htm, Mar. 18, 2008.
Wikipedia: Contact Angle, downloaded from the Internet at: http://en.wikipedia.org/wiki/Contact_angle, Oct. 11, 2007.
KRUSS Drop Shape Analysis System DSA100, downloaded from the Internet at: http://www.kruss.info/instruments/instruments_print/dsa100_e_print.html Nov. 6, 2007.
Yokoyama et al., "Pest Response in Packed Table Grapes to Low Temperature Storage Combined with Slow-Release Sulfur Dioxide Pads in Basic and Large-Scale Tests," J. Econ. Entomol., vol. 94, No. 4, pp. 984-988 (2001).
International Preliminary Report on Patentability for International Application No. PCT/US2009/044495, issued Dec. 2, 2010.
International Preliminary Report on Patentability for International Application No. PCT/US07/11497, completed Aug. 20, 2009.
International Preliminary Report on Patentability for International Application No. PCT/US2009/044495, issued Nov. 23, 2010.
International Search Report for International Application No. PCT/US07/11497, mailed Nov. 16, 2007.
International Search Report for International Application No. PCT/US07/11496, mailed Dec. 5, 2007.
Written Opinion for International Application No. PCT/US07/11496, mailed Dec. 5, 2007.
Written Opinion for International Application No. PCT/US07/11497, mailed Nov. 16, 2007.
Non-Final Office Action mailed Nov. 10, 2010 in co-pending U.S. Appl. No. 11/801,466.
Non-Final Office Action mailed Dec. 16, 2010 in co-pending U.S. Appl. No. 11/801,441.
Hollis, Co-Pending U.S. Appl. No. 11/801,466, filed May 10, 2007.
Rader, Co-Pending U.S. Appl. No. 11/801,441, filed May 10, 2007.
Felsot, A., "Formulation Basics: Inert Ingredients and Why We Need Them", Retrieved from the Internet at: www.ipmnet.org/Tim/Pesticide_Ed/Pesticide_Courses_2008/Cent_OR_Allan_Felsot_1.pdf on Jun. 30, 2009.
International Search Report and Written Opinion for International Patent Application No. PCT/US09/44495, mailed Jul. 13, 2009.
Cowles, et al., "Inert Formulation Ingredients with Activity: Toxicity of Trisiloxane Surfactant Solutions of Two Spotted Spider Mites (Acari: Tetranychidae)", Journal of Economic Entomolgy, vol. 93, No. 2, pp. 180-188 (2000).
Nikolov, et al., "Superspreading Driven by Marangoni Flow", Advances in Colloid Interface Science, vol. 96, pp. 325-338, (2002).
Supplemental European Search Report for EP 07794824.8 dated Nov. 27, 2012.
McKay et al., "Selection of Wetting Adjuvants", Pesticide Formulations and Application Systems: Sixth Volume ASTM STP 943 (1987), pp. 27-30.
Zhang et al., "The spreading and superspeading behavior of new glucosamide-based trisiloxane surfactants on hydrophobic foliage", Colloids and Surfaces A: Physicachemical and Engineering Aspects (2006), vol. 276, pp. 100-106.
European Communication dated Oct. 11, 2013 from corresponding European Application No. 09751366.7 containing an extended European Search Report (8 pages).
Australian Patent Examination Report No. 1 for AU Patent Application 2009249168 issued Sep. 9, 2013.

* cited by examiner

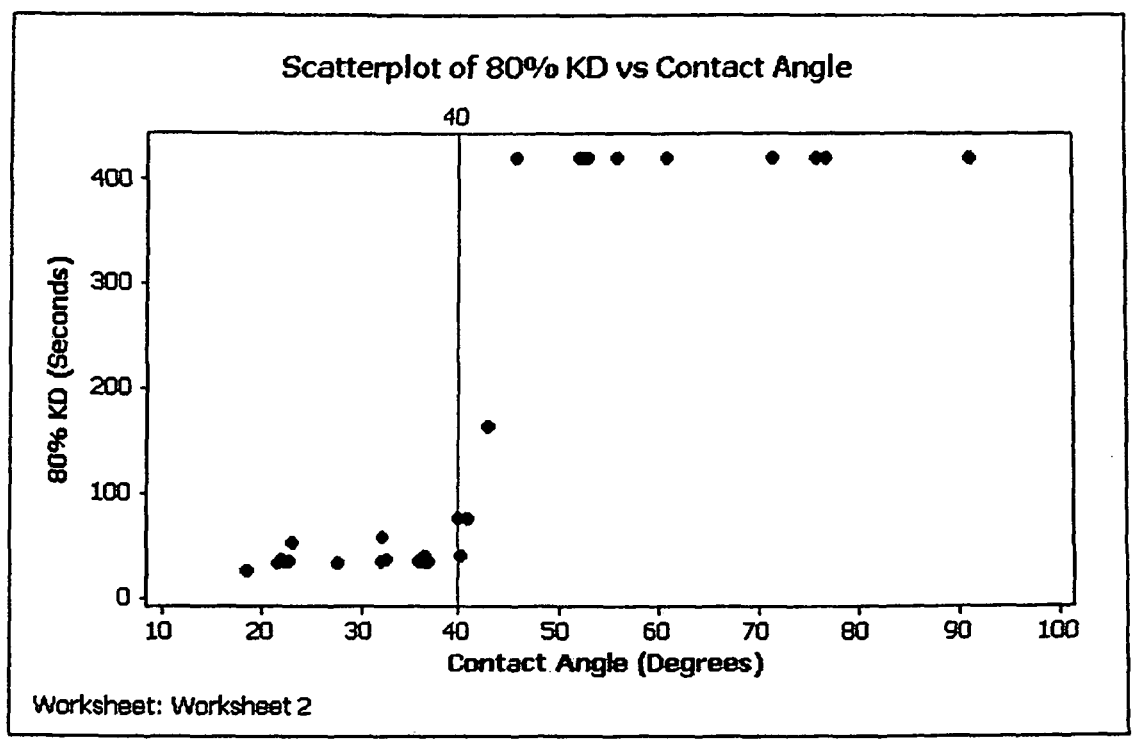

METHODS FOR TREATING ARTHROPODS

CROSS-REFERENCE TO RELATED APPLICATION

This application is a continuation-in-part of application Ser. No. 11/801,466, filed May 10, 2007, which claims the benefit of Provisional Application No. 60/800,545, filed May 15, 2006, and of application Ser. No. 11/801,441, filed May 10, 2007, which claims the benefit of Provisional Application No. 60/800,531, filed May 15, 2006, both of which are incorporated herein in their entirety.

BACKGROUND OF THE INVENTION

1. Field of the Invention

The present invention relates generally to methods for achieving improved pesticidal efficacy in treatment of arthropods. More particularly, the methods of the present invention comprise depositing drops of pesticidal formulations containing at least one surfactant on the surface of treated arthropods to cause enhanced knockdown (KD) effects on the arthropods as a result of the contact angles presented by the drops relative to the surface.

2. Description of Related Art

Pesticidal formulations can be in the form of solutions, emulsions, suspensions, dispersions and the like, and are used in agriculture for applying agricultural chemicals to plants, soil, insects and the like. Among typical pesticidal chemicals are herbicides, insecticides, fungicides, growth regulators and the like.

Such formulations have been known to contain surfactants such as trisiloxane surfactants and other surfactants to enhance the physical characteristics of the formulation for treating pests. For example, in U.S. Pat. No. 6,734,141 ("the '141 patent") and in an article by Cowles et al, entitled "Trisiloxane Surfactant Solutions are Miticidal" which was published in the April, 2000 edition of The Journal of Economic Entomolgy, Vol. 93, no. 2 ("the Cowles et al article"), the use of silicone surfactants, including siloxane surfactants, in agrochemical pesticidal formulations was described.

However, prior pesticidal formulations including those employing surfactants therein such as the formulations described in the '141 patent and in the Cowles et al article have not been sufficiently effective for causing rapid knockdown (KD) of arthropods treated therewith. For example, it has been found that the use of surfactants such as silicone surfactants in agricultural formulations have been only partially effective in causing rapid "knockdown" (KD) of treated arthropods and have been commercially ineffective in causing enhanced knockdown (KD) effects, particularly, in regard to difficult to control pests such as cockroaches.

As employed herein, the expression "enhanced knockdown (KD) effects" refers to the rapid knockdown (KD) of treated arthropods wherein the term "rapid knockdown (KD)" means within a period two (2) minutes or less from the time that at least one drop of the pesticidal formulation is deposited on the surface of an arthropod in which to achieve disruption of mobility of the treated arthropod which normally will lead to mortality of such treated arthropod.

The term arthropod as employed herein means any invertebrate of the phylum Arthropoda including insects, spiders and other arachnids, crustaceans, myriapods and various household pests. For purposes hereof, cockroaches are specifically to be considered to fall within the definition of arthropods.

The deficiency in speed of KD achieved with prior art pesticidal formulations is significant and there has been an on-going need in the consumer market for liquid insecticidal ready-to-use products, which provide fast and effective KD rates of treated arthropods leading to relatively quick mortality (i.e., death) of the treated arthropods.

For example, known formulations often require as much as one-quarter hour or more to achieve acceptable KD rates leading to desired mortality levels against difficult to control pests, such as American cockroaches (*Periplaneta americana*).

Thus, it has been recognized heretofore that it would be advantageous to provide formulations and methods for achieving rapid knockdown of treated arthropods, preferably, resulting in quick kill of the treated arthropods including such difficult to control pests as cockroaches.

For example, it has been recognized that it would be highly beneficial to provide compositions that would achieve KD rates in the order of 80% or greater within about 2 minutes or less and, preferably, within 60 seconds or less, after treatment of the arthropods.

In our copending U.S. patent application Ser. No. 11/801,441, filed May 10, 2007, pesticidal formulations are described that contain surfactants which enable the formulation to have a dynamic surface tension as measured with a Krüss Bubble Pressure Tensiometer (BP2 Version 1.20) which provides enhanced mortality rates (quick kill) of arthropods treated with the formulations.

Furthermore, in our copending U.S. patent application Ser. No. 11/801,466, filed May 10, 2007, silicone surfactant-based agricultural formulations are described containing combinations of silicone surfactants at concentrations sufficient to cause synergistically quick knockdown (KD) levels on treated arthropods.

Nonetheless, it has been found that it would be highly desirable to provide new and improved methods for achieving improved pesticidal effects when formulations containing surfactants such as those disclosed in our above referenced copending applications are deposited on the surface of a treated arthropod such as a cockroach.

In particular, it would be advantageous to provide methods for more effectively employing formulations which contain surfactants, such as certain trisiloxane surfactants and suitable other surfactants, which act to reduce the contact angle of the formulation to a level which enables an effective knockdown (KD) rate within about two minutes or less after the formulation is deposited on a surface of a treated arthropod.

Additionally, it would be advantageous to provide methods for more effectively employing agricultural formulations which contain surfactants, such as certain trisiloxane surfactants and suitable other surfactants, to achieve enhanced knockdown rates, preferably, about 80% or greater, within shorter periods of time when applied to arthropods and particularly to difficult to control arthropods such as cockroaches.

SUMMARY OF THE INVENTION

Accordingly, it is an object of the present invention to provide new and improved methods for achieving markedly improved efficacy in terms of rapid knockdown (KD) of treated arthropods employing formulations containing at least one surfactant therein.

Another object is to provide new and improved methods for treating arthropods, including difficult to control arthropods such as cockroaches, employing formulations containing at least one surfactant wherein the formulation is deposited on a surface of an arthropod at a critical contact angle as measured with a Krüss DSA 100 Contact Angle Measuring System (referred to herein as the "Krüss DSA 100 Tensiometer") to enable enhanced knockdown (KD) of treated arthropods.

A further object is to provide new and improved methods for use of an agricultural product containing at least one surfactant such as a trisiloxane surfactant therein for treatment of arthropods to achieve markedly improved knockdown (KD) efficacy as compared with prior methods.

A still further object is to provide methods for treating arthropods by depositing at least one drop of a pesticidal formulation containing at least one surfactant on a surface of an arthropod at a contact angle sufficient to cause rapid knockdown (KD) of the arthropod.

In particular, it is an object to provide methods for effectively employing formulations which contain surfactants, such as certain trisiloxane surfactants and suitable other surfactants, which act to reduce the contact angle of a drop of the formulation deposited on a solid surface of an arthropod whereby effective arthropod knockdown (KD) rates are achieved.

BRIEF DESCRIPTION OF THE DRAWING

FIG. 1 is a graphical representation depicting a Scatterplot of $80^{th}$ Percentile Cockroach Knockdown (KD) results by Average Contact Angle in seconds after treatment based on the data tabulated in Table 2 of Example 2.

DETAILED DESCRIPTION OF THE INVENTION

In accordance with the present invention, the methods of the present invention for treating arthropods comprise depositing at least one drop of a liquid formulation containing at least one surfactant on a solid surface of an arthropod at a contact angle sufficient to cause rapid knockdown (KD) of the arthropod.

The contact angle comprises an angle formed between a resting drop of the liquid formulation and the solid surface on which the drop rests measured, after a period of about 80 milliseconds (ms) or more from the time that a drop of the liquid formulation is deposited on the solid surface, at a contact point between a tangent line drawn on a liquid/vapor interface surface of the resting drop in contact with the solid surface and a tangent to the solid surface on which the drop rests. Preferably, the contact angle is less than about 400 as measured with a Krüss DSA 100 tensiometer to achieve the desired enhanced knockdown (KD) of treated arthropods.

In particular, the methods of this invention may comprise the steps of providing a liquid formulation containing at least one surfactant in the formulation and depositing the pesticidally active liquid formulation on a solid surface of an arthropod at a contact angle of less than about 40°, as defined previously, which is sufficient to cause rapid knockdown (KD) of the arthropod (i.e., within about two minutes or less after at least one drop of the formulation is deposited on the solid surface) and to cause arthropods having the at least one drop of the pesticidally active liquid formulation deposited thereon to exhibit a knockdown (KD) rate of about 80% or greater within such period of time.

In accordance with the present invention the formulations contain at least one surfactant, such as a silicone surfactant including certain trisiloxane surfactants, or suitable other surfactants such as ethoxylated acetylenic diol and pyrrolidone surfactants and mixtures thereof.

These surfactants act to reduce the contact angle of the formulations to the critical level of about 40° or less, as measured with a Krüss DSA 100 Tensiometer, after a period of about 80 milliseconds (ms) or more from the time that a drop of the formulation is deposited on the solid surface whereby enhanced and effective arthropod knockdown (KD) rates are achieved within about two minutes or less after depositing the formulation on the surface.

More specifically, the contact angle of the formulations may range from about 0° up to about 40°, as measured with the Krüss DSA 100 Tensiometer in a period of greater than about 80 milliseconds (ms) after the drop is deposited on the solid surface up to a time at which the drop is completely wetted on the solid surface, to achieve a desired arthropod knockdown (KD) rate of greater than about 80% within a period of about two minutes or less after the formulation is deposited on the solid surface.

As defined herein, the contact angle is an angle formed between a resting drop of pesticidally active liquid or fluid and a solid surface corresponding to a solid surface of a treated arthropod on which the liquid or fluid drop is applied. The contact angle is measured at a contact point between a tangent line drawn on a liquid/vapor interface surface of the pesticidal drop in contact with a solid surface corresponding to the surface of the arthropod and a tangent to such solid surface.

In other words, the contact angle between a drop of a pesticidal formulation deposited on a solid surface and such solid surface, as measured with a Krüss DSA 100 Tensiometer, is an angle formed between the outline tangent to the drop's liquid/vapor interface surface and the solid surface.

More particularly, the contact angle at which the liquid/vapor interface of a drop meets the solid surface of an arthropod and which is required to achieve the desired rapid KD effects of the present invention has been found to be specific for any given system. This critical contact angle for any given system is determined by the interaction across the drop/surface interface although it has been determined that the contact angle must be less than about 40° to achieve the herein desired results.

The Krüss DSA 100 Tensiometer referred to herein for measurement of the relevant contact angle of the drop of formulation on a particular surface comprises a commercially available contact angle measuring system identified as the DSA 100 Contact Angle Measuring System (referred to herein as "the DSA 100 Tensiometer") sold by Krüss GmbH (Hamburg, Germany) utilizing Krüss "DSA 3" software also sold by Krüss GmbH (Hamburg, Germany). A detailed description of the DSA 100 Contact Angle Measuring System and the accompanying DSA 3 software which enables static and dynamic contact angle measurements on liquid drops in a gaseous phase, among other uses, has been described in a copyrighted publication entitled "KRÜSS DSA3 Software for prop Shape Analysis Installation and Operation Manual V1-04, Krüss GmbH, Hamburg, Germany 2005" which is incorporated herein by reference.

Thus, in accordance with the present invention, new and improved methods are provided for treating arthropods, including difficult to control arthropods such as cockroaches, employing pesticidal formulations containing at least one surfactant wherein the formulations are deposited on a solid surface of an arthropod at a critical angle as measured with a Krüss DSA 100 Tensiometer within a period of greater than about 80 milliseconds (ms) after a drop of the formulation is deposited on the surface.

Exemplary surfactants which are suitable for use, alone or in combination, as the at least one surfactant to be incorporated in the formulations employed in the methods of the present invention are the surfactants tabulated as follows:

| Surfactant Trade Names | Surfactant Class | Exemplary Vendor |
|---|---|---|
| Silwet REACH | Trisiloxane ethoxylate (hydroxyl end cap) | Momentive Performance Materials |
| Silwet L-77 | Trisiloxane ethoxylate (methyl end cap) | Momentive Performance Materials |
| Silwet 806 | Trisiloxane | Momentive Performance Materials |
| Agrimax 3 | 2-pyrrolidinone, 1-octyl; 2-pyrrolidinone, 1-ethenylhexadecyl, homopolymer | ISP Agrochemicals |
| TMulz 1227 | Phospate Ester | Harcros Chemicals Inc. |
| Ethylan TD-60 | Tridecyl alcohol (6EO) ethoxylate | AkzoNobel Surface Chemistry LLC |
| Lankropol 4500 | Sodium Dioctyl sulfosuccinate (70% in ethanol/water) | AkzoNobel Surface Chemistry LLC |
| Silwet 806 | Trisiloxane alkoxylate (EO/PO) | Momentive Performance Materials |
| Dynol 604 | 2,5,8,11 tetramethyl 6 dodecyn-5,8 diol ethoxylate | Air Products and Chemicals, Inc. |
| Surfynol 465 | Ethoxylated 2,4,7,9-tetramethyl 5 decyn-4,7-diol | Air Products and Chemicals, Inc. |

Preferably, the at least one surfactant is selected from the group consisting of trisiloxane, ethoxylated acetylenic diol and pyrrolidone surfactants and mixtures thereof.

In a most preferred embodiment, the at least one surfactant in the formulation is a trisiloxane surfactant selected from the group consisting of:

$$CH_3-\underset{\underset{CH_3}{|}}{\overset{\overset{CH_3}{|}}{Si}}-O-\underset{\underset{\underset{\underset{O-[CH_2-CH_2-O]_y-CH_3}{|}}{CH_2}}{\underset{CH_2}{|}}}{\overset{\overset{CH_3}{|}}{Si}}-O-\underset{\underset{CH_3}{|}}{\overset{\overset{CH_3}{|}}{Si}}-CH_3$$

wherein y=8; and $$CH_3-\underset{\underset{CH_3}{|}}{\overset{\overset{CH_3}{|}}{Si}}-O-\underset{\underset{\underset{\underset{O-[CH_2-CH_2-O]_y-H}{|}}{CH_2}}{\underset{CH_2}{|}}}{\overset{\overset{CH_3}{|}}{Si}}-O-\underset{\underset{CH_3}{|}}{\overset{\overset{CH_3}{|}}{Si}}-CH_3$$

wherein y=8;
and mixtures thereof.

In order to provide a desired rapid rate of KD of treated arthropods, the formulation used in the method of this invention preferably includes at least one surfactant that causes the contact angle of the formulation to be at a level of 40° or less, preferably in a range of from about 0° up to about 40°, as measured with a Kruss DSA 100 Tensiometer in a period of greater than about 80 milliseconds (ms) after the drop is deposited on the solid surface up to a time at which the drop is completely wetted on the solid surface, to achieve a desired arthropod knockdown (KD) rate, preferably, greater than about 80% within a period of about two minutes or less after the formulation is deposited on the solid surface of a treated arthropod In a preferred embodiment, the at least one surfactant is incorporated in the formulations employed in the methods of the present invention at a concentration of about 0.1 weight percent to about 1.5 weight percent.

For enhanced knockdown (KD) results, it is most preferred that the at least one surfactant in the formulations employed in the methods of the present invention composition is selected from the group consisting of Silwet L-77® and Silwet REACH® (also known as Silwet 408®), Silwet 806® and mixtures thereof.

As a result of the rapid knockdown (KD) effects achieved in treating arthropods with drops of a formulation deposited on the solid surface of a treated arthropod at a particular contact angle, it has been found that very effective agricultural products, including liquid pesticidal products, can be provided which will fulfill needs in the consumer market for pesticidal products which provide better knockdown (KD) rates, particularly when used for treatment of difficult to control arthropods, such as cockroaches. Specifically, we have found that the formulations of the present invention must contain a sufficient concentration of surfactant to cause the contact angle of drops deposited on the arthropod surface to be about 40° or less, as measured with a Krüss DSA 100 Tensiometer.

As noted above, a detailed description of the construction and operation of the Krüss DSA 100 Tensiometer employed for measuring the critical contact angle for achieving the desired rapid KD results in accordance with the present invention is provided in a Krüss GmbH publication entitled "KRÜSS DSA3 Software for prop Shape Analysis Installation and Operation Manual V1-04, KRÜSS GmbH, Hamburg, Germany 2005" which is incorporated herein by reference.

In regard to measurement of the critical contact angle for achieving required rapid KD rates herein, it should be noted that for purposes of convenience and to enable more accurate and reproducible numerical correlation of angular determinations, solid test surfaces comprising Parafilm® M barrier film coated smooth, planar surfaces were employed as substitutes for the actual solid arthropod surfaces in determining and measuring the critical contact angles.

This procedure for angular determination was performed in accordance with standard methodologies such as those followed heretofore for observation of effective contact angles of droplets of formulations for treatment of leaves (e.g., see "Pesticide Formulations and Application Systems", 18th Volume, published 1998, by John D. Nalewaja et al, at pages 282-283).

Specifically, Parafilm® M coated surfaces were employed to provide an accurate representation of the waxy exoskeleton of an arthropod and, thus, enabled measurement of the critical contact angles of the drops of the formulations tested herein to achieve required KD efficacy. The resulting angular contact determinations made on Parafilm® M coated surfaces were found to correlate directly with the observed results when such formulations were applied on the solid surface the arthropods.

In general, agricultural spray mixtures contain water and an active agricultural chemical ingredient, such as a pesticide (including herbicides, insecticides, fungicides, growth regulators and the like). Typically, at least 50 percent of a pesticidal spray mixture is composed of water. Optionally, the pesticidal spray mixture can contain at least one component selected from the group consisting of organic surfactants, antifoam agents and organic solvents. Agricultural spray mixtures are commercially available as ready-to-use products or can be prepared in a containment vessel from an agricultural chemical concentrate, water, and optionally one or more surfactants and/or antifoaming agents.

The amount of an active ingredient (i.e., agricultural chemical) in a spray mixture, if used in addition to the at least one surfactant employed in the formulations for use in the method of the present invention as described above, will be any amount effective for the intended purpose, but typically will range from about 0.001 to about 5 percent by weight based upon the total weight of the agricultural spray mixture (e.g., from about 0.03 percent to about 0.5 percent, preferably from about 0.05 percent to about 0.25 percent based upon the total weight of the agricultural spray mixture). The bulk of the remainder of the agricultural spray mixture is comprised of water.

Surfactants, solvents, biocides, antifoam agents, antifreezes, pH modifiers, colorants, nutrients and plant growth regulators may be included in the formulations to achieve desired results.

Illustrative pesticides which can be employed as an active ingredient in the pesticidal spray mixtures of the present invention, in addition to the at least one surfactant described herein, include those from the groups consisting of herbicides, insecticides, fungicides, miticides and the like.

The following specific examples are presented to further illustrate and explain certain aspects of the present invention. However, the examples are set forth for illustration only, and are not to be construed as limiting on the present invention. In the following examples, all percentages and parts are by weight unless otherwise specified.

EXAMPLE 1

Test formulations for use in this Example 1 were prepared by introducing and mixing the surfactant/surfactants specified in Table 1 below in water at the concentrations indicated therein and the contact angles resulting when drops of these formulations were deposited on solid surfaces corresponding to the solid exoskeleton surface of an arthropod were measured according to the procedure set forth herein below and the average contact angles derived from this testing are set forth in the following Table 1:

TABLE 1

Average Contact Angle after 80 Milliseconds (Surfactants in Water)

| | CONCENTRATION (Weight %) | | | | |
|---|---|---|---|---|---|
| SURFACTANT | 0.05% | 0.10% | 0.50% | 1.00% | 1.50% |
| Silwet REACH | 51.7 | 42.8 | 23.1 | 22.2 | 42.4 |
| Silwet L-77 | 60.8 | 26.4 | 27.6 | 21.5 | 23.7 |
| Silwet REACH/Silwet L-77 | 52.7 | 36.4 | 21.9 | 18.4 | 22.8 |
| Agrimax 3 | 76.9 | 69.6 | 45.7 | 36.9 | 35.9 |
| Tmulz 1227 | 71.4 | 57.2 | 40.2 | 36.9 | 32.0 |
| Ethylan TD-60 | 55.7 | 51.9 | 42.9 | 40.0 | 40.9 |
| Ethylan NS-500LQ | 68.0 | 65.9 | 57.3 | 52.8 | 48.7 |
| Lankropol 4500 | 72.1 | 60.7 | 38.3 | 32.5 | 30.1 |
| Silsurf D208 | 91.2 | 90.6 | 77.2 | 75.9 | 75.8 |
| Zonyl FSO | 72.6 | 68.8 | 55.6 | 55.1 | 53.1 |
| Sliwet 806 | 56.7 | 49.5 | 32.2 | 34.7 | 34.4 |
| Dynol 604/Surfynol 465 | 52.3 | 44.8 | 36.4 | 33.7 | 35.7 |

The procedure employed for measuring the contact angles of drops of the herein tested formulations comprised:

Step 1: A testing chamber of a Kruss DSA 100 Tensiometer wherein the test measurements of this example were taken was set to a 60% relative humidity (RH) at a temperature of 25° C. prior to measurement and recording of results. The testing chamber conditions were checked prior to each measurement since they must fall within the range of 55% to 65% RH and 24° C. to 26° C. The gas carrier flow into the testing chamber was set at the lowest setting to achieve the desired humidity level.

Step 2: The solid testing surfaces for use in this test were prepared by covering the surfaces of glass slides with parafilm and introducing these parafilm coated glass slide testing surfaces into the testing chamber. The coated surfaces were determined to be smooth and level when placed into the testing chamber.

Step 3: The mixtures of water and the tested surfactant/surfactants were prepared by mixing the ingredients to form homogeneous test sample solutions.

Step 4: Each of the test sample solutions was drawn up into a syringe with a Teflon needle insert, making sure the syringe and needle were triple rinsed with the solution to be tested prior to applying the final sample to the solid testing surface. It was important to minimize the time the solution was in the syringe prior to taking the measurement, especially if the solution separates easily.

Step 5: The needle diameter was measured to enable calculation of the magnification factor.

Step 6: The needle was then lowered into the testing chamber of the Krüss DSA 100 Tensiometer and the focus and illumination within the chamber was adjusted to achieve optimal video image.

Step 7: Then, individual test samples were dispensed from the syringe through the needle onto the solid testing surfaces at 6.32 microliters per minute until a drop of the test sample fell onto the test surface. This action was recorded on video camera at a rate of 25 frames per second.

Step 8: The first point of contact between each of the liquid samples and the solid testing surface was determined using the recorded video. This first contact was denoted as T=0 or time zero.

Step 9: The video was advanced two frames forward, or 80 milliseconds (ms) and the contact angle was measured using the Height-Width (HW) calculation method described at page 150 under the heading "16.3.3.3 Height-width method" in "KRÜSS DSA1 v1.9 prop Shape Analysis for DSA 100" User Manual V 1.9-03, KRÜSS GmbH, Hamburg, Germany 2004". In accordance with this method, the height and width of the drop shape are determined. If the contour line enclosed by a rectangle is regarded as being a segment of a circle, then the contact angle can be calculated from the height-width relationship of the enclosing rectangle. The smaller drop volume, the more accurate the approximation for smaller drops are more similar to the theoretically assumed spherical cap form.

Step 10: Steps 1-9 were repeated for each test solution until five clear, measurable videos were achieved on multiple sample surfaces.

Step 11: The contact angle data resulting from this testing was recorded as the average contact angle resulting from the five repeat tests referenced in Step 10 above as set forth in Table 1 above.

EXAMPLE 2

Test formulations for use in this Example 2 were prepared in accordance with the procedures described in Example 1 whereby the surfactant/surfactants specified in Table 2 below were introduced and mixed in water at the concentrations indicated in the table. Then, the resulting test formulations were screened for knockdown efficacy by a procedure comprising introducing American cockroaches into 1.5-inch diameter polyvinyl chloride (PVC) pipe sections with aluminum crumb cups affixed to the bottom end of the pipe sections. An automatic pipetter was used to apply 4.8 ml of each of the tested pesticidal formulations to each cockroach. Excess liquid was drained from the tubes through the crumb cups. After treatment, each cockroach was transferred to a clean polypropylene testing container. Each cockroach was individually observed until knockdown occurred. A cockroach was determined to be knocked down when it had lost its ability to control movement about the testing container, typically followed by rapid mortality.

After drops of the test formulations containing the various surfactants and concentrations of surfactants were deposited on the solid exoskeleton surfaces of the cockroaches, the time intervals (in seconds) to achieve treated cockroach Knockdown (KD) rates of 80% at various contact angles (average of five replicated samples) were measured in accordance with the above screening procedure and the results achieved correlating average contact angle determinations for tested surfactant formulations versus 80% arthropod (cockroach) knockdown (KD) are illustrated in Table 2 as follows:

In accordance with the tabulated test results in Table 2 which were achieved by application of drops of the test formulations in accordance with the herein described screening procedure, it was determined that a correlation exists whereby it can be accurately deduced from the results achieved when surfactant containing formulations are applied at an average contact angle of about 40° or less on a Parafilm® M coated glass surface, that such formulations when applied to cockroaches would achieve rapid knockdown (KD) of at least 80% of the treated cockroaches within two minutes or less after treatment.

To the contrary, it was found that those tested surfactant containing formulations exhibiting contact angles greater than about 40° employing the above outlined test procedure did not demonstrate comparable at least 80% enhanced knockdown (KD) effects within such two minutes or less period after application to cockroaches.

Thus, based on the results tabulated in Table 2 above as well as the $80^{th}$ Percentile scatterplot diagrammatic representation of the tabulated data from Table 2 as illustrated in FIG. 1 herein, it has been demonstrated that test formulations containing at least one surfactant deposited on the solid surfaces of arthropods such as cockroaches at contact angles of less than about 40° provide Knockdown (KD) rates of 80% or greater within a period of less than about two (2) minutes whereas formulations containing at least one surfactant which are deposited on the solid surfaces of arthropods such

TABLE 2

| Surfactant(s) and Surfactant Concentration(s) in Test Formulations (% by Weight) | Average Contact Angle (Measured 80 Milliseconds after the Test Formulations Were Applied on Solid Surfaces of Treated Cockroaches) Expressed in Degrees (0) | 80% KD (Seconds after Application of Test Formulation on Treated Cockroaches) |
|---|---|---|
| 0.50% Tmulz 1227 in water | 40.2 | 40 |
| 1.50% Ethylan TD-60 in water | 40.9 | 77 |
| 1.00% Ethylan TD-60 in water | 40.0 | 76 |
| 1.0% Agrimax 3 in water | 36.9 | 36 |
| 0.05% Silwet REACH/0.05% Silwet L-77 in water | 36.4 | 40 |
| 0.25% Dynol 604/0.25% Surfynol 465 in water | 36.4 | 35 |
| 1.5% Agrimax 3 in water | 35.9 | 36 |
| 1.0% Lankropol 4500 in water | 32.5 | 37 |
| 0.50% Silwet 806 in water | 32.2 | 58 |
| 1.5% Tmulz 1227 in water | 32.0 | 35 |
| 0.50% Silwet L-77 in water | 27.6 | 34 |
| 0.50% Silwet REACH in water | 23.1 | 53 |
| 0.75% Silwet REACH/0.75% Silwet L-77 in water | 22.8 | 36 |
| 1.00% Silwet REACH in water | 22.2 | 36 |
| 0.25% Silwet REACH/0.25% Silwet L-77 in water | 21.9 | 37 |
| 1.00% Silwet L-77 in water | 21.5 | 33 |
| 0.5% Silwet REACH/0.5% L-77 in water | 18.4 | 26 |
| 0.50% Ethylan TD-60 in water | 42.9 | 164 |
| 0.05% Silsurf D208 in water | 91.2 | 420 |
| 0.05% Agrimax 3 in water | 76.9 | 420 |
| 1.0% Silsurf D208 in water | 75.9 | 420 |
| 0.05% Tmulz 1227 in water | 71.4 | 420 |
| 0.05% Silwet L-77 in water | 60.8 | 420 |
| 0.1% Lankropol 4500 in water | 60.7 | 420 |
| 0.05% Ethylan TD-60 in water | 55.7 | 420 |
| 0.5% Zonyl FSO in water | 55.6 | 420 |
| 0.025% Silwet REACH plus 0.025% Silwet L-77 in water | 52.7 | 420 |
| 0.025% Dynol 604 plus 0.025% Surfynol 465 in water | 52.3 | 420 |
| 0.1% Ethylan TD-60 in water | 51.9 | 420 |
| 0.50% Agrimax 3 in water | 45.7 | 420 | as cockroaches at contact angles of about 40° or higher require substantially longer periods of time (up to about 7 minutes or longer) to achieve comparable Knockdown (KD) rates of 80% or greater. Of course, such extended periods for achieving effective KD rates would be functionally and commercially unacceptable whereas the shorter terms to achieve high KD rates achieved with the methods and compositions of the present invention would be highly desirable both functionally and commercially.

Although the invention has been described in its preferred forms with a certain degree of particularity, it is to be understood that the present disclosure has been made by way of example only. Numerous changes in the details of the compositions and ingredients therein as well as the methods of preparation and use will be apparent without departing from the spirit and scope of the invention, as defined in the appended claims.

What is claimed is:

1. A method of treating cockroaches comprising the steps of:
   (a) providing an aqueous composition comprising an agent,
     wherein the agent is a liquid surfactant,
     wherein said liquid surfactant is 2,5,8,11 tetramethyl 6 dodecyn-5,8 diol ethoxylate; ethoxylated 2,4,7,9-tetramethyl 5 decyn-4,7-diol; or mixtures thereof,
     wherein the agent is present at a concentration of about 0.1% weight percent to about 1.5% weight percent and
     wherein the agent forms a contact angle that is less than about 40° as measured with a Krüss DSA 100 tensiometer, such that the contact angle is formed by a resting drop of the liquid composition on a solid surface and rests for a period of greater than about 80 milliseconds after depositing;
   (b) depositing at least one drop of the composition onto a solid surface of a cockroach; and
   (c) causing the cockroach, with the at least one drop of the composition deposited thereon, to exhibit a rapid knockdown (KD), at a rate of about 80% within about two minutes or less after the at least one drop is deposited.

2. A method of treating cockroaches comprising the steps of:
   (a) providing an aqueous composition comprising an agent,
     wherein the agent is a liquid surfactant,
     wherein said liquid surfactant is

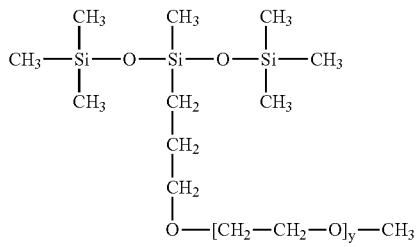

wherein y=8; or

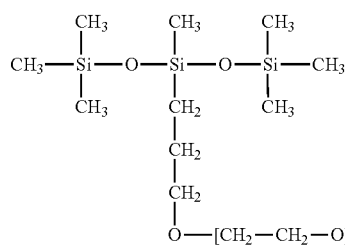

wherein y=$^8$; and mixtures thereof,
     wherein the agent is present at a concentration of about 0.1% weight percent to about 1.5% weight percent; and
     wherein the agent forms a contact angle that is less than about 400 as measured with a Krüss DSA 100 tensiometer, such that the contact angle is formed by a resting drop of the liquid composition on a solid surface and rests for a period of greater than about 80 milliseconds after depositing;
   (b) depositing at least one drop of the composition onto a solid surface of a cockroach; and
   (c) causing the cockroach, with the at least one drop of the composition deposited thereon, to exhibit a rapid knockdown (KD), at a rate of about 80% within about two minutes or less after the at least one drop is deposited.

* * * * *

UNITED STATES PATENT AND TRADEMARK OFFICE
CERTIFICATE OF CORRECTION

| | | |
|---|---|---|
| PATENT NO. | : 8,790,673 B2 | Page 1 of 1 |
| APPLICATION NO. | : 12/154105 | |
| DATED | : July 29, 2014 | |
| INVENTOR(S) | : Shannon Hollis et al. | |

It is certified that error appears in the above-identified patent and that said Letters Patent is hereby corrected as shown below:

IN THE CLAIMS

In claim 2, column 12, line 34, delete "400" and insert --40°--.

Signed and Sealed this
Seventh Day of April, 2015

Michelle K. Lee
*Director of the United States Patent and Trademark Office*